012
United States Patent [19]

Helsley et al.

[11] 4,287,212

[45] Sep. 1, 1981

[54] 2-ARYL-1,2-DIALKYLCYCLOALKYLA-MINES

[75] Inventors: Grover C. Helsley, Pottersville, N.J.; Horst Dornauer, Kelkheim, Fed. Rep. of Germany; Larry Davis, Flemington, N.J.

[73] Assignee: American Hoechst Corporation, Bridgewater, N.J.

[21] Appl. No.: 881,529

[22] Filed: Feb. 27, 1978

Related U.S. Application Data

[63] Continuation of Ser. No. 682,133, Apr. 30, 1976, abandoned.

[51] Int. Cl.³ .................... A01N 33/02; A01N 37/30; C07C 87/50
[52] U.S. Cl. ............................... 424/330; 260/501.1; 260/501.18; 424/316; 564/219; 564/307
[58] Field of Search ............... 260/570.5 CA, 501.18, 260/501.1; 424/330, 316; 564/307

[56] References Cited

U.S. PATENT DOCUMENTS

| | | | |
|---|---|---|---|
| 2,520,516 | 8/1950 | Zoeren | 260/570.5 X |
| 3,499,901 | 3/1970 | Hellerbach | 260/570.5 X |
| 3,573,304 | 3/1971 | Eberle et al. | 260/570.6 X |
| 3,652,589 | 3/1972 | Flick et al. | 260/570.5 X |
| 3,657,244 | 4/1972 | Mentrup et al. | 260/570.5 X |
| 3,979,444 | 9/1976 | Lednicer | 260/570.5 X |

OTHER PUBLICATIONS

Takahashi et al., "Chemical Abstracts", vol. 52, pp. 10909–10914 (1958).

*Primary Examiner*—Robert V. Hines
*Attorney, Agent, or Firm*—Curtis, Morris & Safford

[57] ABSTRACT

Novel 2-aryl-1,2-dialkylcycloalkylamines, physiologically tolerable acid addition salts thereof, and a method of preparing the same are described. These compounds are useful as analgesic and diuretic agents.

8 Claims, No Drawings

2-ARYL-1,2-DIALKYLCYCLOALKYLAMINES

This is a continuation, of application Ser. No. 682,133 filed Apr. 30, 1976 and now abandoned.

This invention relates to novel 2-aryl-1,2-dialkylcycloalkylamines which are useful as analgesics, physiologically tolerable acid addition salts thereof, methods of preparing same, methods of treatment with pharmaceutically effective amounts thereof, and to pharmaceutical compositions containing such compounds as essential active ingredients. Additionally, compounds of this invention are further useful as diuretics.

To the best of our knowledge, the compounds of the present invention have not heretofore been described or suggested. 2-Aryl-2-alkylcyclohexylamines described in Neth. Appl. No. 6,609,050 (Jan. 2, 1967), 2-arylcycloheptylamines described by A. Burger, et al., [Science 112, 306 (1950)], and 2,2-diaryl- cyclopentylamines described by S. H. Graham, [J. Chem. Soc., C, 390 (1969)] represent the closest prior art and are clearly outside the scope of and do not suggest the compounds of the present invention.

The 2-aryl-1,2-dialkylcycloalkylamines of this invention conform to the formula

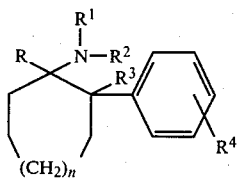

in which R, $R^1$ and $R^3$ are loweralkyl, $R^2$ is hydrogen, loweralkyl, cycloalkylloweralkyl of from 4 to 8 carbon atoms, phenylloweralkyl, benzoylloweralkyl or alkenyl of from 3 to 6 carbon atoms, $R^4$ is hydrogen, methoxy or hydroxy, and n is an integer from 0 to 2. When $R^2$ is phenylloweralkyl or benzoylloweralkyl the phenyl ring may be substituted by halogen, methoxy, hydroxy, trifluoromethyl or loweralkyl. In the above definitions, loweralkyl means those radicals of from 1 to 4 carbon atoms. Compounds which are useful as diuretic agents are those wherein $R^4$ represents methoxy or hydroxy.

Acids useful for preparing the acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

Compounds of this invention are prepared by one of three multi-step sequence of reactions as described below. With the exceptions noted, R, $R^1$, $R^2$ and $R^3$ and n are as defined earlier, and X is halogen, preferably chlorine or bromine.

Method A

1. A compound of the formula

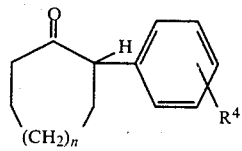

wherein $R^4$ is H or alkoxy, is prepared by the reaction of a 2-halocycloalkylketone with the appropriate Grignard reagent under normal conditions. Alternatively, lithium compounds can be utilized instead of a normal Grignard reagent.

2. A compound of formula I is alkylated by a method known to the art to give a compound of the formula

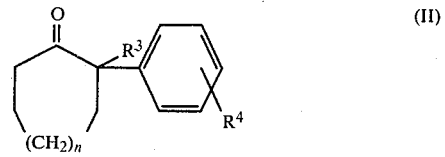

One such method is abstracting the proton which is α to both the carbonyl and the phenyl group and forming an alkali metal salt of the resulting carbanion by use of sodium hydride in an organic solvent such as benzene, at a temperature from ambient to the boiling point of the solvent, for from a few minutes to several hours. The salt is alkylated with an alkyl halide of the formula $R^3X$, in the same solvent, at a temperature from ambient to the boiling point of the solvent for a sufficient time which permits total alkylation.

3. A Grignard reagent of the formula RMgX is reacted with a compound of formula II under normal Grignard conditions to give a cycloalkanol of the formula

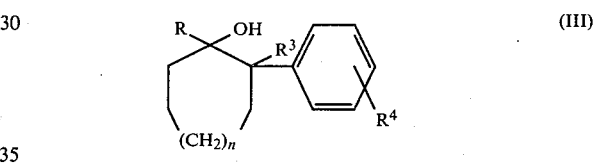

4. A compound of the formula III is reacted with sodium cyanide or an alkyl nitrile under the conditions of the Ritter reaction to form an amide compound of the formula

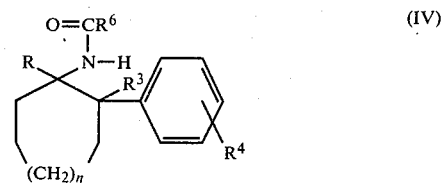

wherein $R^6$ is hydrogen or alkyl of from 1 to 3 carbon atoms. A preferred method utilizes sulfuric acid in glacial acetic acid as the solvent at a temperature of from ambient to 75° C., for from several minutes to 24 hours.

5. The above amide of formula IV is reduced to provide a secondary amine of the formula:

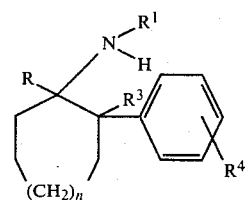

A preferred method utilizes lithium aluminum hydride as the reducing agent in the presence or absence of an organic solvent, for from a few minutes to 60 hours at a temperature from ambient to the boiling point of the solvent.

6. An above secondary amine is converted to a tertiary amine of the formula

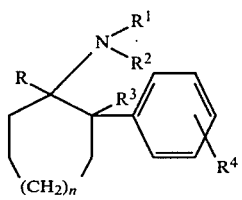

VI by alkylation with an alkyl halide in the absence or presence of a suitable solvent such as n-butanol, with or without a catalyst such as potassium iodide with or without an acid scavenger such as potassium carbonate for from 30 minutes to 72 hours at a temperature from ambient to 150° C. Another method is methylation via the Eschweiler-Clark Reaction. Also methylation can be effected by the addition of an aqueous solution of formaldehyde to a solution of the secondary amine in a suitable solvent and permitting the mixture to react at a temperature of from −20° C. to the boiling point of the solvent for a few minutes to 24 hours and then introducing a reducing agent, such as sodium borehydride, providing the desired tertiary amine.

Alternatively a secondary amine of formula V can be reacted with a carbonyl halide of the formula $R^7COX$ wherein $R^7$ represents phenyl, cycloalkyl or alkyl in the presence of a suitable solvent such as chloroform, with or without an acid scavenger such as triethylamine, at a temperature of from 20° to 75° C. to give a corresponding N-carbonyl compound of the formula

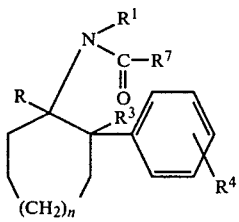

VII

Reduction of the carbonyl by any convenient method known to the art provides a corresponding tertiary amine of formula VI.

Additionally, a secondary amine can be reacted with a compound of the formula

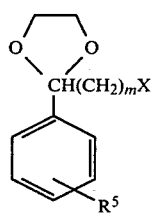

wherein m is an integer from 1 to 3 and $R^5$ is hydrogen, halogen, methoxy, hydroxy, trifluoromethyl or loweralkyl with a suitable solvent such as n-butanol, an acid scavenger such as triethylamine or potassium carbonate and a catalyst or reaction initiator such as a few crystals of potassium iodide at a temperature of from ambient to the reflux temperature of the solvent followed by a period of acid hydrolysis to give a corresponding tertiary amine of formula VI in which $R^2$ is benzoylloweralkyl of the formula

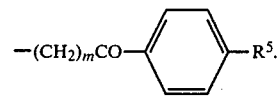

Method B

1. A compound of formula III can be dehydrated to give a cycloalkene of the formula

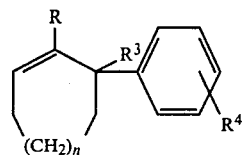

VIII

A preferred method of dehydrating is by the addition of a solution of sulfuric acid in a glacial acetic acid and permitting the mixture to react at a temperature of from 0° to 70° C. for from 30 minutes to 24 hours.

2. An above cycloalkene is treated according to Steps 4 through 6 of Method A to give a compound of the invention.

Method C

A compound of the formulae V or VI wherein $R^4$ is alkoxy can be dealkylated to give a corresponding phenolic compound of the invention, preferably with a concentrated hydrobromic acid at a temperature from ambient to 110° C., for from a few minutes to several hours.

It will be readily appreciated by those skilled in the art that the time and temperature required to complete the reaction in any of the preceeding methods are interrelated and dependent upon structures and compositions of the reaction components and the solvent, if any.

The compounds of the present invention are useful as analgesic agents due to their ability to alleviate pain in mammals. The analgesic activity of compounds of this invention is demonstrated in the phenyl-2-quinone induced writhing assay in mice, a standard assay for analgesia [Proc. Soc. Exptl. Biol. Med., 95, 729 (1957)]. Thus, for instance, an approximately 50% inhibition of writhing is effected by a 12 mg/kg subcutaneous dose of 2-(3-hydroxyphenyl)-N,N,1,2-tetramethylcyclopentylamine hydrochloride. The analgesic activity in this test of additional compounds of this invention is shown in Table I.

TABLE I

| COMPOUND | SUBCUTANEOUS DOSE (mg/kg) | ORAL DOSE (mg/kg) | % INHIBITION OF WRITHING |
|---|---|---|---|
| N,2-dimethyl-1-ethyl-N-(3-methyl-2-butenyl)-2-phenylcyclohexyl amine . oxalate . hemihydrate | 13.5 | | 50 |
| N,2-dimethyl-1-ethyl-2-(3-methoxyphenyl)-cyclohexylamine . oxalate . hydrate | 15 | 50 | 50 52 |
| 2-(3-methoxyphenyl)-N,N,1,2-tetramethylcyclohexylamine | 26 | 50 | 50 41 |
| 2-(3-methoxyphenyl)-N,1,2-trimethylcyclo- | 25 | | 38 |

TABLE I-continued

| COMPOUND | SUBCUTANEOUS DOSE (mg/kg) | ORAL DOSE (mg/kg) | % INHIBITION OF WRITHING |
|---|---|---|---|
| heptylamine . hydrochloride . hemihydrate | | | |
| N,2-dimethyl-1-ethyl-2-(3-hydroxyphenyl)-cyclohexylamine . hemioxalate | 25 | | 43 |
| 1-ethyl-2-(3-hydroxyphenyl)-N,N,2-trimethylcyclohexylamine . hydrochloride | 25 | | 49 |
| 2-(3-methoxyphenyl)-N,1,2-trimethylcyclohexylamine | 25 | | 52 |
| 2-(3-methoxyphenyl)-N,N,1,2-tetramethylcyclopentylamine . hydrochloride | 25 | | 63 |
| 1-ethyl-2-(4-hydroxyphenyl)-N,N,2-trimethylcyclohexylamine . hydrochloride . hemihydrate | 25 | 50 | 69 52 |
| 1-ethyl-N,N,2-trimethyl-2-phenylcyclohexylamine | 50 | | 92 |
| 2-(3-hydroxyphenyl)-N,N-1,2-tetramethylcyclohexylamine . hydrochloride | | 50 | 46 |

For comparison, aspirin and propoxyphene hydrochloride, known analgesic agents, effect a 34% and 50% inhibition of writhing with doses of 60 mg/kg. These data illustrate that the compounds of the invention are useful for the alleviation of pain in mammals when administered in amounts ranging from about 0.1 to 100 mg/kg of body weight per day.

Compounds of the invention are further useful as diuretic agents due to their ability to produce diuresis in mammals. Diuretic activity is measured in rats by a method described by C. M. Kagawa and M. J. Kalm, Arch. Intern. Pharmacodyn., 137, 241 (1962). Drugs are dosed orally to a group of rats and the average volume excreted in compared to (divided by) the average volume excreted by a positive control group of rats dosed orally with 1000 mg/kg of urea, a known diuretic agent. The resulting drug/urea ratios, if greater than one, are indicative of diuretic activity. The diuretic activity in this test of representative compounds of this invention and of chlorthiazide, a standard diuretic, is shown in Table II.

TABLE II

| COMPOUND | DOSE (mg/kg) | DRUG/UREA RATIO |
|---|---|---|
| 1-ethyl-2-(4-methoxyphenyl)-N,N,2-trimethylcyclohexylamine . hydrochloride . hemihydrate | 50 | 2.5 |
| 1-ethyl-2-(4-hydroxyphenyl)-N,N,2-trimethylcyclohexylamine . hydrochloride . hemihydrate | 50 | 2.2 |
| 2-(3-methoxyphenyl)-N,N,1,2-tetramethylcyclopentylamine . hydrochloride | 50 | 2.1 |
| 2-(3-hydroxyphenyl)-N,N,1,2-tetramethylcyclopentylamine . hydrochloride | 50 | 1.6 |
| 1-ethyl-2-(3-hydroxyphenyl)-N,N,2-trimethylcyclohexylamine . hydrochloride | 50 | 1.6 |
| chlorthiazide | 50 | 1.3 |

The above data illustrates that compounds of the present invention are useful for producing diuresis when administered to mammals at doses of from about 0.1 to 100 mg/kg of body weight.

Further examples of compounds of the invention are:
N,2-dimethyl-2-phenyl-1-propylcyclohexylamine;
N-benzoylethyl-1-(n-butyl)-N,2-dimethyl-2-phenylcyclohexylamine;
N-cyclohexylmethyl-2-(2-hydroxyphenyl)-N,1,2-trimethylcycloheptylamine;
N-benzyl-N,2-dimethyl-1-ethyl-2-phenylcyclohexylamine;
2-(2-methoxyphenyl)-N,N,1,2-tetramethylcyclopentylamine;
N,2-dimethyl-1-ethyl-N-[3-(4-hydroxybenzoyl)propyl]-2-(4-hydroxyphenyl) cyclohexylamine;
N,2-dimethyl-1-ethyl-2-(4-hydroxyphenyl)-N-(4-trifluoromethylbenzoylmethyl)cyclopentylamine;
N-cyclopentylethyl-2-(2-methoxyphenyl)-N,1,2-trimethylcyclohexylamine;
N-[3-(4-hydroxybenzoyl)propyl]-2-(4-hydroxphenyl)-N,1,2-triethylcyclohexylamine;
2-(n-butyl)-2-phenyl-N,N,1-trimethylcyclopentylamine;
2-(n-propyl)-2-(4-hydroxyphenyl)-N,N,1-trimethylcyclohexylamine; and
N,N-dimethyl-1-ethyl-2-phenyl-2-propylcyclopentylamine.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose or oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as surose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For the purpose of parenteral therapeutics administration, the active compounds of the invention may be incorporated into a solution or suspension. These preparations should contain at least 0.1% of active compound, but may be varied to be between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The invention is further illustrated by the following examples:

EXAMPLE 1 a. A mixture of 261.8 g of 3-methoxybromobenzene in 500 ml of ether is added dropwise to a 34.0 g sample of magnesium in 600 ml of ether. To the reaction mixture is added a suitable catalyst and the mixture is heated vigorously to initiate the reaction. The prepared Grignard Reagent is cooled in an ice bath while 185.6 g of 2-chlorocyclohexanone in 500 ml of ether is introduced. The ether is removed and xylene added and the xylene solution is refluxed for 1 hour. The solution is poured over ice and dilute hydrochloric acid, the organic layer separated, the aqueous layer extracted with benzene, the organic layer and benzene extracts are combined and washed with dilute sodium hydroxide solution, dried, filtered, and the solvent removed leaving a red oil. The oil is vacuum distilled to give a clear pink liquid of 2-(3-methoxyphenyl)cyclohexanone.

b. A solution of 71.5 g of 2-(3-methoxphenyl)cyclohexanone in 150 ml of benzene is added dropwise to a suspension of 19.2 g of sodium hydride (50% in oil) in 200 ml of benzene. The mixture is allowed to stand for 5 hours and it is then refluxed with vigorous stirring for 20 minutes. The mixture is allowed to cool and 71.0 g of methyliodide in 100 ml of benzene is added and refluxed for 13 hours. The excess sodium hydride is decomposed with water, the benzene layer separated and dried and the benzene removed. The residue is distilled to give a liquid, b.p. 131°–133° C./0.6 mm of 2-(3-methoxyphenyl)-2-methylcyclohexanone.

Analysis: Calculated for $C_{14}H_{18}O_2$: 77.02%C; 8.31%H. Found: 77.42%C; 8.66%H.

c. A solution of 31 of ethyliodide in 50 ml of ether is added dropwise to 4.9 g of magnesium in 100 ml of ether. The reaction is initiated with heat and then the reaction rate maintained by addition. After total addition the reaction is refluxed for 1 hour. The reaction mixture is cooled with an ice-bath, a solution of 30 g of 2-(3-methoxyphenyl)-2-methylcyclohexanone in 50 ml of benzene added portionwise and the mixture is refluxed for 20 hours. The mixture is allowed to cool, poured into an ice cold ammonium chloride solution, stirred for 10 minutes and extracted with ether. The ether extract is washed with water, dried, filtered and the solvent removed leaving a yellow oil which is vacuum distilled to give the oil, b.p. 121°–127° C./0.3 mm, of 1-ethyl-2-(3-methoxyphenyl)-2-methylcyclohexanol. Thin layer chromatography, infrared and nuclear magnetic resonace determinations confirms the assigned structure.

Analysis: Calculated for $C_{16}H_{24}O_2$: 77.37%C; 9.74%H. Found: 77.01%C; 9.22%H.

d. To a mixture of 25 ml of glacial acetic acid, 49.6 g of 1-ethyl-2-(3-methoxyphenyl)-2-methylcyclohexanol and 10.6 g of 95% sodium cyanide is added portionwise with stirring a solution of 50 g of concentrated sulfuric acid in 25 ml of glacial acetic acid. The temperature is maintained at 50° to 60° C. during the addition of the sulfuric acid. The reaction mixture is allowed to stand overnight to ambient temperature, poured into 500 ml of water, neutralized with a 15% aqueous sodium hydroxide solution, and extracted with ether. The combined ether extracts are dried, the ether and other volatiles distilled off to give a yellow resin which is triturated with ether to produce a solid product, of 1-ethyl-2-(3-methoxphenyl)-2-methylcyclohexylformamide.

e. To a refluxing solution of 8.4 g of lithium aluminum hydride in 100 ml of tetrahydrofuran is added dropwise a solution of 31.0 g of 1-ethyl-2 -(3-methoxyphenyl)-2-methylcyclohexylformamide in 50 ml of tetrahydrofuran. The reaction mixture is refluxed for 20 hours, cooled, quenched with a saturated ammonium chloride solution, diluted with ether, and filtered. The organic layer is separated, washed with water, dried, filtered, and the solvent removed leaving a yellow oil. The oil is converted to an oxalate salt. which is recrystallized from an isopropanol-ether mixture to give the salt, m.p. 132° C., of N,2-dimethyl-1-ethyl-2-(3-methoxyphenyl)-cyclohexylamine oxalate hydrate.

Analysis: Calculated for $C_{17}H_{27}NO.(CO_2H)_2.H_2O$: 61.77%C; 8.46%H; 3.79%N. Found: 61.76%C; 7.82%H; 3.87%N.

EXAMPLE 2 a. 1,2-dimethyl-2-phenylcyclohexylformamide is obtained from its appropriate starting materials and intermediates by following the manipulative procedures of Examples 1 a through d.

Analysis: Calculated for $C_{15}H_{21}NO$: 77.88%C; 9.15%H; 6.06%N. Found: 78.32%C; 9.27%H; 6.10%N.

b. 7.5 g of 1,2-dimethyl-2-phenylcyclohexylformamide is placed in a Soxhlet extractor and slowly added to a suspension of 3.0 g of lithium aluminum hydride in 300 ml of ether. After total addition the mixture is refluxed for 48 hours. The reaction mixture is allowed to cool and quenched with water and 15% aqueous sodium hydroxide. The ether layer is separated, dried and then removed leaving an oil. The oil is converted to the hydrochloride which is recrystallized from an isopropanol-ether mixture to give white crystals, mp 228°-299° C., of N,1,2-trimethyl-2-phenylcyclohexylamine hydrochloride.

Analysis: Calculated for $C_{15}H_{23}N \cdot HCl$: 70.98%C; 9.53%H; 5.52%N. Found: 70.72%C; 9.59%H; 5.58%N.

EXAMPLES 3-8

By following the procedures similar to the procedure outlined above in Example 1e, the compounds 2-(3-methoxyphenyl)-N,1,2-trimethylcyclohexylamine (Example 3), 1-ethyl-N,2-dimethyl-2-phenylcyclohexylamine (Example 4), 2-(3-methoxyphenyl)-N,1,2-trimethylcyclopentylamine (Example 5), 2-(3-methoxyphenyl)-N,1,2-trimethylcycloheptylamine (Example 6), 2-(4-methoxyphenyl)-N,1,2-trimethylcyclohexylamine (Example 7), and 1-ethyl-2-(4-methoxyphenyl)-N,2-dimethylcyclohexylamine (Example 8) and furher identified below in Table II are obtained by the reduction of 1,2-dimethyl-2-(3-methoxyphenyl)cyclohexylformamide, 1-ethyl-2-methyl-2-phenylcyclohexylformamide, 1,2-dimethyl-2-(3-methoxyphenyl)cyclopentylformamide, 1,2-dimethyl-2-(3-methoxyphenyl) cycloheptylformamide, 1,2-dimethyl-2-(4-methoxphenyl)cyclohexylformamide and 1-ethyl-2-methyl-2-(4-methoxphenyl)-cyclohexylformamide, respectively.

These formamides are obtained from their appropriate starting materials and intermediates by following the manipulative procedures of Example 1, steps a through d.

TABLE III

| Ex. | Empirical Formula | Recryst'n Solvent | m.p./b.p.(mm) °C. | Calc'd % C | Calc'd % H | Calc'd % N | Found % C | Found % H | Found % N |
|---|---|---|---|---|---|---|---|---|---|
| 3 | $C_{16}H_{25}NO$ | — | 138-141/0.5 mm | 77.68 | 10.18 | 5.66 | 77.60 | 10.24 | 5.65 |
| 4 | $C_{16}H_{25}N$ | — | 84-86/0.3 mm | 83.05 | 10.89 | — | 82.53 | 10.73 | — |
| 5 | $C_{15}H_{23}NO \cdot HCl$ | isopropanol $Et_2O$ | 171-172 | 66.77 | 8.97 | 5.19 | 66.55 | 9.09 | 5.09 |
| 6 | $C_{17}H_{27}NO \cdot HCl \cdot \frac{1}{2}H_2O$ | isopropanol $Et_2O$ | 145 | 66.53 | 9.53 | 4.57 | 66.62 | 9.25 | 4.36 |
| 7 | $C_{16}H_{25}NO$ | — | | 77.68 | 10.18 | 5.66 | | | |
| 8 | $C_{17}H_{27}NO$ | — | — | 61.77 | 8.46 | 3.79 | | | |

EXAMPLE 9

2 ml of a 37% solution of formaldehyde in water are added to a solution of 2.2 g of N,2-dimethyl-1-ethyl-2-phenylcyclohexylamine (Example 4) in 40 ml of methanol and the reaction solution is stirred for one hour at ambient temperature and then refluxed for 30 minutes. The solution is allowed to cool and 1.5 g of sodium borohydride are added portionwise. After total addition the solution is stirred at ambient temperature for one hour and refluxed for an additional hour. Ice is added to the solution, it is extracted with methylene chloride, the combined methylene chloride extracts are dried and the solvent is removed, leaving a yellow oil which is distilled under reduced pressure to give the liquid, b.p. 92°-94° C./0.25 mm, of 1-ethyl-2-phenyl-N,N,2-trimethylcyclohexylamine.

Analysis: Calculated for $C_{17}H_{27}N$: 83.22%C; 11.09%H. Found: 82.87%C; 10.79%H.

EXAMPLE 10

By following the manipulative procedure as described above in Example 9, N,1,2-trimethyl-2-phenylcyclohexylamine, free base of Example 2, is treated to produce an oil of 2-phenyl-N,N,1,2-tetramethylcyclohexylamine. The hydrochloride is made which is recrystallized twice from isopropanol to give the salt as white crystals, mp 277°-278° C., dec.

Analysis: Calculated for $C_{16}H_{26}ClN$: 71.75%C; 9.79%H; 5.23%N. Found: 70.83%C; 9.62%H; 5.42%N.

EXAMPLE 11

To a solution of 3.0 g of N,1,2-trimethyl-2-(3-methoxyphenyl)cyclohexylamine, Example 3, in 50 ml of methanol is added 3 ml of a 37% solution of formaldehyde in water. The reaction solution is stirred at amblent temperature for 14 hours and then at reflux for an additional hour. The solution is allowed to cool and 2.0 g of sodium borohydride is added portionwise. After total addition the solution is stirred for three hours, then refluxed for one hour, the methanol removed and ice-water added to the residue. The mixture is extracted with methylene chloride, dried, solvent removed and distilled to give the liquid, b.p. 133°-136° C./0.3 mm, of 2-(3-methoxyphenyl)-N,N,1,2-tetramethylcyclohexylamine.

Analysis: Calculated for $C_{17}H_{27}NO$: 78.11%C; 10.41%H; 5.36%N. Found: 78.55%C; 10.31%H; 5.65%N.

EXAMPLE 12

By following the manipulative procedure described above in Example 11, 2-(3-methoxyphenyl)-N,1,2-trimethylcycloheptylamine, free base of Example 6, is methylated to provide 2-(3-methoxyphenyl)-N,N,1,2-tetramethylcycloheptylamine.

EXAMPLE 13

To a solution of 8.0 g of 2-(3-methoxyphenyl)-N,1,2-trimethylcyclopentylamine, Example 5, in 10 ml of cold a 97% aqueous formic acid is added 9 ml of 37% aqueous formaldehyde solution. The reaction solution is stirred at ambient temperature for a few minutes and the heated at 90° C. until evolution of carbon dioxide gas begins. The heat is removed and after evolution ceases the reaction is stirred at 95°-100° C. for 7 hours. The reaction is cooled, 30 ml of 4 N aqueous hydrochloric acid added and the reaction mixture evaporated to one half of its volume, the pH is adjusted to 10 with sodium hydroxide solution and extracted with ether. The combined ether extracts are washed with water, dried, filtered and the ether removed leaving a yellow oil which is converted to the hydrochloride. The salt is recrystallized from an isopropanol-ether mixture to give the product, mp 210° C., dec, of 2-(3-methoxyphenyl)-N,N,1,2-tetramethylcyclopentylamine hydrochloride.

Analysis: Calculated for $C_{16}H_{25}NO \cdot HCl$: 67.70%C; 9.23%H; 4.94%N. Found: 67.82%C; 8.69%H; 4.86%N.

EXAMPLE 14

By following the manipulative procedure described above in Example 13, N,2-dimethyl-1-ethyl-2-(3-methoxyphenyl)cyclohexylamine, free base of Example 1, is treated to produce a yellow oil which is converted to an oxalate salt. The salt is recrystallized from an isopropanol-ether mixture to give the product, mp 125° C., of 1-ethyl-2-(3-methoxyphenyl-N,N,2-trimethylcyclohexylamine oxalate hydrate.

Analysis: Calculated for $C_{18}H_{29}NO.(CO_2H)_2.H_2O$: 62.64%C; 8.67%H; 3.65%N. Found: 62.93%C; 7.68%H; 3.55%N.

EXAMPLE 15

To a solution of 17.0 g of N,2-dimethyl-1-ethyl-2-(4-methoxyphenyl)cyclohexylamine, Example 8, in 20 ml of cold 97% aqueous formic acid is added 18 ml of a 37% aqueous formaldehyde solution and the mixture is stirred at 100° C. for 8 hours. The mixture is allowed to cool and then poured into 100 ml of a 4 N aqueous hydrochloric acid, stirred for 10 minutes and washed with ether. The aqueous layer is basified with sodium hydroxide solution, extracted with ether, the ether washed with water, dried and filtered and the ether removed leaving a brown oil which is converted to a hydrochloride. The salt is recrystallized from an isopropanol-ether mixture to give the product, mp 105° C., dec., of 1-ethyl-2-(4-methoxyphenyl)-N,N,2-trimethylcyclohexylamine hydrochloride hemihydrate.

Analysis: Calculated for $C_{18}H_{29}NO.HCl.\frac{1}{2}H_2O$: 67.37%C; 9.74%H; 4.37%N. Found; 67.52%C; 9.31%H; 4.52%N.

EXAMPLE 16

A solution of 5.2 g of 2-(3-methoxyphenyl)-N,1,2-trimethylcyclohexylamine, Example 3, 3.1 g of allyl bromide, 20.0 g of anhydrous potassium carbonate and a few crystals of potassium iodide in 100 ml of n-butanol is prepared. After the solution is stirred at 120° C. for 20 hours it is allowed to cool, filtered and the solvent removed leaving a dark oil which is dissolved in ether, the ether solution washed with water, dried, filtered and the solvent removed leaving a dark oil which is converted to an oxalate salt. The salt is recrystallized twice from an ethyl acetate-ether mixture to give the product, mp 115° C., dec, of N-allyl-2-(3-methoxyphenyl)-N,1,2-trimethylcyclohexylamine oxalate hydrate.

Analysis: Calculated for $C_{19}H_{29}NO.(CO_2H)_2.H_2O$: 63.78%C; 8.41%H; 3.54%N. Found: 63.46%C; 7.78%H; 3.43%N.

EXAMPLE 17

A solution of 4.3 g of N,2-dimethyl-1-ethyl-2-phenylcyclohexylamine, Example 4, 3.7 g of 1-bromo-3-methyl-2-butene, 20.0 g of potassium carbonate and a few crystals of potassium iodide is prepared. The solution is stirred at 120° C. for 72 hours, cooled, filtered and the solvent removed leaving a brown semi-solid which is stirred with 300 ml of water for 10 minutes and extracted with ether. The combined ether extracts are washed with water, dried and filtered and the ether removed leaving a yellow oil which is converted to an oxalate salt. The salt is recrystallized twice from ethyl acetate to give the product, mp 150°-152° C., of N,2-dimethyl-1-ethyl-N-(3-methyl-2-butenyl)2-phenylcyclohexylamine oxalate hemihydrate.

Analysis: Calculated for $C_{21}H_3N.(CO_2H)_2.\frac{1}{2}H_2O$: 69.31%C; 9.11%H; 3.52%N. Found: 68.82%C; 8.72%H; 3.61%N.

EXAMPLE 18

To a cold solution of 2.0 g of N,2-dimethyl-1-ethyl-2-phenylcyclohexylamine, Example 4, and 1.0 g of triethylamine in 25 ml of chloroform is added dropwise a solution of 1.2 g of cyclopropylcarbonyl chloride in 25 ml of chloroform. The reaction mixture is stirrd at ambient temperature for 20 hours, washed with water, dried and the chloroform removed leaving a brown oil. The oil is dissolved in 25 ml of tetrahydrofuran and added dropwise to a refluxing mixture of lithium aluminum hydride in 50 ml of dry tetrahydrofuran. Refluxing is continued for 20 hours, the mixture cooled, quenched with saturated ammonium chloride solution, diluted with ether and filtered. The organic layer is collected, washed with water, dried, filtered and the solvent removed leaving a yellow oil which is converted to a hydrochloride which is recrystallized from an isopropanol-ether mixture to give the product, mp 103° C., dec., of N-cyclopropylmethyl-N,2-dimethyl-1-ethyl-2-phenylcyclohexylamine hydrochloride hemihydrate.

Analysis: Calculated for $C_{20}H_{31}N.HCl.\frac{1}{2}H_2O$: 72.58%C; 10.05%H; 4.23%N. Found: 72.45%C; 10.03%H; 4.12%N.

EXAMPLE 19

A mixture of 5.0 g of N,2-dimethyl-1-ethyl-2-(3-methoxyphenyl)-cyclohexylamine, free base of Example 1, and 30 ml of 48% of aqueous hydrogen bromide solution is heated on a steam bath for 3 hours. The mixture is diluted with water, the pH adjusted to 8 with concentrated ammonium hydroxide and extracted with ether. The combined ether extracts are washed with water, dried, and filtered and the ether removed leaving a brown oil which is converted to an oxalate salt. The salt is recrystallized from an isopropanol-ether mixture to give the product, mp 125° C., dec., of N,2-dimethyl-1-ethyl-2-(3-hydroxyphenyl)cyclohexylamine hemioxalate hemihydrate.

Analysis: Calculated for $C_{16}H_{25}NO.\frac{1}{2}(CO_2H)_2.\frac{1}{2}H_2O$: 67.74%C; 9.03%H; 4.65%N. Found: 67.22%C; 8.34%H; 4.57%N.

EXAMPLES 20-25

By following the manipulative procedure described in Example 19, the phenolic compounds 2-(3-hydroxyphenyl)-N,N,1,2-tetramethylcyclohexylamine (Example 20), 2-(3-hydroxyphenyl)-N,N,1,2-tetramethylcycloheptylamine (Example 21), 2-(3-hydroxyphenyl)-N,N,1,2-tetramethylcyclopentylamine (Example 22), 1-ethyl-2-(3-hydroxyphenyl)-N,N,2-trimethylcyclohexylamine (Example 23), 1-ethyl-2-(4-hydroxyphenyl)-N,N,2-trimethylcyclohexylamine (Example 24), and 2-(3-hydroxyphenyl)-N,1,2-trimethylcycloheptylamine (Example 25) are produced. The starting materials and other relevant data for these compounds are indicated in Table IV.

TABLE IV

| Ex. | Starting Material | Empirical Formula | Recryst'n Solvent | m.p.°C. | Calc. %C | Calc. %H | Calc. %N | Found %C | Found %H | Found %N |
|---|---|---|---|---|---|---|---|---|---|---|
| 20 | Ex. 11 | $C_{16}H_{25}NO \cdot HCl$ | isopropanol Et$_2$O | 140 | 67.70 | 9.23 | 4.94 | 67.90 | 8.59 | 4.70 |
| 21 | Ex. 12 | $C_{17}H_{27}NO \cdot (CO_2H)_2$ | isopropanol | 170, dec. | 64.93 | 8.32 | 3.99 | 64.90 | 8.04 | 3.08 |
| 22 | Ex. 13 | $C_{15}H_{23}NO \cdot HCl$ | isopropanol | 260, dec. | 66.77 | 8.97 | 5.19 | 67.06 | 8.51 | 5.08 |
| 23 | Ex. 14 | $C_{17}H_{27}NO \cdot HCl$ | Isopropanol-ether | 175, dec. | 68.55 | 9.47 | 4.70 | 67.93 | 8.82 | 4.22 |
| 24 | Ex. 15 | $C_{17}H_{27}NO \cdot HCl \cdot \frac{1}{2}H_2O$ | isopropanol-ether | 115, dec. | 66.53 | 9.52 | 4.57 | 66.79 | 9.25 | 4.48 |
| 25 | Ex. 5 | $C_{14}H_{21}NO$ | — | — | | | | | | |

EXAMPLE 26

To a cooled mixture of 2-(3-hydroxyphenyl)-N,1,2-trimethylcyclopentylamine, Example 25, and 7.1 g of triethylamine in 50 ml of chloroform is added a solution of 5.5 g of acetyl chloride in 25 ml of chloroform. The mixture is stirred at ambient temperature for 20 hours and at 65° C. for 4 additional hours, cooled, washed with water, dried and filtered. The solvent is removed leaving a brown oil which is dissolved in 50 ml of tetrahydrofuran and added to a refluxing suspension of lithium aluminum hydride in 100 ml of tetrahydrofuran. The reaction mixture is refluxed at 75° C. for 20 hours, cooled, quenched with aqueous saturated ammonium chloride solution, diluted with ether, filtered and the organic layer collected, washed with water, dried and filtered. The solvent is removed leaving a brown oil which is converted to a hydrochloride which is recrystallized twice from an isopropanol-ether mixture to give the product, mp 110° C., dec., of N-ethyl-2-(3-hydroxyphenyl)-N,1,2-trimethylcyclopentylamine hydrochloride.

Analysis: Calculated for $C_{16}H_{25}NO \cdot HCl$: 67.70%C; 9.23%H; 4.94%N. Found: 67.44%C; 9.34%H; 4.86%N.

EXAMPLE 27 a. To a cooled mixture of 1,2-dimethyl-2-(3-methoxyphenyl)cyclohexanol in 25 ml of glacial acetic acid is added dropwise a solution of 25 g of concentrated sulfuric acid in 15 ml of glacial acetic acid while maintaining the reaction temperature at 55° C. After total addition the reaction mixture is stirred at ambient temperature for 20 hours and then poured into ice-water. The pH is adjusted to 8 with sodium hydroxide solution and extracted with ether. The combined ether extracts are washed with water and dried and the ether removed leaving a yellow residue. The residue is vacuum distilled and the fraction that distills at 115°-120° C./0.5 mm is 2,3-dimethyl-3-(3-methoxyphenyl)cyclohexene. Thin layer chromatography and infrared and nuclear magnetic resonance spectroscopy determinations confirm the assigned structure.

Analysis: Calculated for $C_{15}H_{20}O$: 83.28%C; 9.32%H. Found: 82.99%C; 9.54%H.

b. By following the manipulative procedures described above in Example 1d and e, a sample of 2,3-dimethyl-3-(3-methoxyphenyl)cyclohexene is treated to give the product, bp 138°-141° C./0.5 mm, 2-(3-methoxyphenyl)-N,1,2-trimethylcyclohexylamine.

Analysis: Calculated for $C_{16}H_{25}NO$: 77.68%C; 10.18%H; 5.66%N. Found; 77.60%C; 10.24%H; 5.65%N.

EXAMPLE 28 a. To a cooled mixture of 15 g of 1,2-dimethyl-2-(3-methoxyphenyl)cyclopentanol in 25 ml of glacial acetic acid is added dropwise a solution of 25 g of concentrated sulfuric acid in 15 ml of glacial acetic acid while maintaining the reaction temperature at 0°-5° C. After total addition the mixture is stirred at ambient temperature for 2 hours, cooled, diluted with 300 ml of water and extracted with chloroform. The combined chloroform removed leaving a yellow oil which is vacuum distilled to give the product, mp 80°-81° C./0.15 mm, of 2,3-dimethyl-3-(3-methoxyphenyl)cyclopentene.

b. By following the manipulative procedures described above in Example 1d and e, a sample of 2,3-dimethyl-3-(3-methoxyphenyl)cyclopentene is treated to produce a yellow oil of 2-(3-methoxyphenyl)-N,1,2-trimethylcyclopentylamine which is converted to its hydrochloride salt and recrystallized from an isopropanol-ether mixture to afford the product, mp 171°-172° C.

Analysis: Calculated for $C_{15}H_{23}NO \cdot HCl$: 66.77%C; 8.97%H; 5.19%N. Found: 66.55%C; 9.09%H; 5.09%N.

EXAMPLE 29

To a cold solution of 4.3 g of N,2-dimethyl-1-ethyl-2-phenylcyclohexylamine, Example 4, and 2.5 g of triethylamine in 35 ml of chloroform is added dropwise with stirring a solution of 3.8 g of phenylacetyl chloride in 25 ml of chloroform. After total addition the reaction mixture is stirred at ambient temperature for 24 hours, then washed with water and dried. The mixture is filtered and the solvent removed leaving a yellow oil. The oil is dissolved in 20 ml of tetrahydrofuran and this solution then added to a refluxing suspension of 1.52 g of lithium aluminum hydride in 100 ml of tetrahydrofuran. After refluxing is continued for 20 hours the reaction is permitted to cool and is then quenched with 60 ml of an ammonium chloride solution, diluted with ether and filtered. The organic layer is collected, washed with water and dried. The organic mixture is filtered and the solvent removed leaving another yellow oil which is converted to an oxalate salt and recrystallized from an isopropanol-ether mixture to give the salt, dec at 85° C., of N,2-dimethyl-1-ethyl-N-phenethyl-2-phenylcyclohexylamine.oxalate.dihydrate.

Analysis: Calculated for $C_{24}H_{33}N \cdot (CO_2H)_2 \cdot 2H_2O$: 67.65%C; 8.52%H; 3.03%N. Found: 68.06%C; 7.85%H; 2.81%N.

EXAMPLE 30 a. A sample of 2-(3-methoxyphenyl)-N,1,2-trimethylcyclohexylamine, Example 3, is demethylated according to the procedure outlined above in Example 19 to produce 2-(3-hydroxyphenyl)-N,1,2-trimethylcyclohexylamine.

b. To a cold solution of 4.5 g of 2-(3-hydroxyphenyl)-N,1,2-trimethylcyclohexylamine and 4.0 g of triethylamine in 50 ml of chloroform is added dropwise with stirring a solution of 4.75 g cyclobutylcarbonylchloride in 25 ml of chloroform. After total addition stirring is continued at ambient temperature for 48 hours, and then the mixture is washed with water and dried. The mixture is filtered and the solvent removed leaving an orange oil which is dissolved in 50 ml of tetrahydrofuran and this solution added to a refluxing suspension of 1.90 g of lithium aluminum hydride in 100 ml of tetrahydrofuran. Refluxing is continued for 20 hours and then the reaction mixture is permitted to cool, quenched with 50 ml of an ammonium chloride solution and diluted with ether. The biphasic mixture is filtered and the organic layer is collected, washed with water, dried and filtered. The solvent is removed leaving a yellow oil which is converted to a hydrochloride salt and recrystallized twice from an isopropanol-ether mixture to give the product, mp 155° C., of N-cyclobutylmethyl-2-(3-hydroxyphenyl)-N,1,2-trimethylcyclohexylamine.hydrochloride.hemihydrate.

Analysis: Calculated for $C_{20}H_{31}NO.HCl.\frac{1}{2}H_2O$: 69.24%C; 9.59%H; 4.04%N. Found: 69.28%C; 9.60%H; 3.98%N.

EXAMPLE 31 a. A sample of N,2-dimethyl-1-ethyl-2-(4-methoxyphenyl)cyclohexylamine, Example 8, is demethylated according to the procedure outlined above in Example 19 to produce N,2-dimethyl-1-ethyl-2-(4-hydroxyphenyl)cyclohexylamine.

b. A reaction mixture of 4.4 g of N,2-dimethyl-1-ethyl-2-(4-hydroxyphenyl)cyclohexylamine, 4.9 g of γ-chloro-4-fluorobutyprophenone ethylene glycol ketal, 20 g of anhydrous potassium carbonate, and a few crystals of potassium iodide in 100 ml of n-butanol is refluxed at 120° for 72 hours. The reaction mixture is allowed to cool, filtered and the filtrate evaporated leaving a dark residue. The residue is dissolved in a combined solvent of 100 ml of ethanol and 100 ml of a 3 N hydrogen chloride solution, allowed to stand 3 hrs, the pH adjusted to 12 with sodium hydroxide and then this alkaline solution is stirred for 1 hour and extracted with benzene. The combined benzene extracts are washed with water, dried, and filtered and the solvent removed leaving a dark oil. The oil is converted to an oxalate salt which is recrystallized from an isopropanol-ether mixture to give the product, dec. 105° C., of N,2-dimethyl-1-ethyl-N-[3-(4-fluorobenzoyl)propyl]-2-(4-hydroxyphenyl)cyclohexylamine.oxalate.dihydrate.

Analysis: Calculated for $C_{26}H_{34}FNO_2.(CO_2H)_2.2H_2O$: 62.55%C; 7.50%H; 2.61%N. Found: 62.85%C; 6.83%H; 2.79%N.

We claim:

1. A compound of the formula:

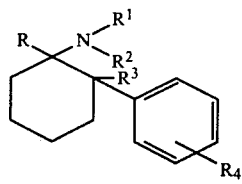

where
R, $R^1$ and $R^3$ are lower alkyl,
$R^2$ is alkenyl of three to six carbon atoms,
and $R^4$ is hydrogen, methoxy or hydroxyl, or a physiologically tolerable acid addition salt of said compound.

2. A compound as defined in claim 1 wherein R is methyl or ethyl, $R^1$ and $R^3$ are methyl and $R^2$ is allyl or 3-methyl-2-butenyl.

3. A compound as defined in claim 2 wherein $R^4$ is methoxy or hydroxy.

4. The compound defined in claim 1 which is N,2-dimethyl-1-ethyl-N-(3-methyl-2-butenyl)-2-phenylcyclohexylamine.

5. The compound defined in claim 1 which is N-allyl-2-(3-methoxyphenyl)-N,1,2-trimethyl-cyclohexylamine.

6. A pharmaceutical composition which comprises between 0.5 and about 70% by weight of a compound defined in claim 1 as an essential active ingredient, the balance being a pharmaceutically acceptable carrier therefor.

7. A method of treating pain which comprises administering to a patient a pharmaceutically effective amount of a compound defined in claim 1.

8. A method of producing diuresis which comprises administering to a patient a physiologically effective amount of a compound defined in claim 1.

* * * * *